United States Patent
Shiobara et al.

(10) Patent No.: US 9,963,542 B2
(45) Date of Patent: May 8, 2018

(54) SILICONE-MODIFIED EPOXY RESIN, COMPOSITION CONTAINING THE EPOXY RESIN, AND CURED PRODUCT OF SAME

(71) Applicants: Shin-Etsu Chemical Co., Ltd., Tokyo (JP); Nippon Kayaku Kabushiki Kaisha, Tokyo (JP)

(72) Inventors: Toshio Shiobara, Tokyo (JP); Junichi Sawada, Gunma (JP); Miyuki Wakao, Gunma (JP); Tsutomu Kashiwagi, Gunma (JP); Naofusa Miyagawa, Tokyo (JP); Yoshihiro Kawada, Tokyo (JP); Chie Sasaki, Tokyo (JP); Naosuke Taniguchi, Tokyo (JP)

(73) Assignees: Shin-Etsu Chemical Co., Ltd. (JP); Nippon Kayaku Kabushiki Kaisha (JP)

( * ) Notice: Subject to any disclaimer, the term of this patent is extended or adjusted under 35 U.S.C. 154(b) by 0 days. days.

(21) Appl. No.: 15/300,645

(22) PCT Filed: Mar. 25, 2015

(86) PCT No.: PCT/JP2015/059119
§ 371 (c)(1),
(2) Date: Sep. 29, 2016

(87) PCT Pub. No.: WO2015/151957
PCT Pub. Date: Oct. 8, 2015

(65) Prior Publication Data
US 2017/0107322 A1 Apr. 20, 2017

(30) Foreign Application Priority Data
Mar. 31, 2014 (JP) .................. 2014-071020

(51) Int. Cl.
*C08G 59/38* (2006.01)
*C08G 59/32* (2006.01)
*C08G 59/42* (2006.01)

(52) U.S. Cl.
CPC ......... *C08G 59/3281* (2013.01); *C08G 59/38* (2013.01); *C08G 59/4238* (2013.01); *C08G 59/4269* (2013.01); *C08G 59/4284* (2013.01)

(58) Field of Classification Search
None
See application file for complete search history.

(56) References Cited

U.S. PATENT DOCUMENTS 5,492,981 A 2/1996 Hoehn et al.
6,815,520 B2 11/2004 Yoneda et al.
(Continued)

FOREIGN PATENT DOCUMENTS

JP 7-97433 A 4/1995
JP 2002-265787 A 9/2002
(Continued)

OTHER PUBLICATIONS

Osamu Hara, ThreeBond Technical News "Curing Agents for Epoxy Resin" Dec. 20, 1990, 10 pages.*
(Continued)

*Primary Examiner* — Robert S Loewe
(74) *Attorney, Agent, or Firm* — Wood, Phillips, Katz, Clark & Mortimer

(57) ABSTRACT

A silicone-modified epoxy resin which yields a cured product having low gas permeability and excellent strength; a composition of the silicone-modified epoxy resin; and an epoxy resin cured product obtainable by curing the composition, are provided.

An epoxy resin represented by the following Formula (1):

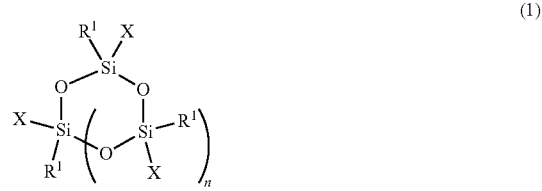

(1)

wherein $R^1$ represents a hydrocarbon group having 1 to 6 carbon atoms; X represents an organic group having a norbornane epoxy structure, or a hydrocarbon group having 1 to 6 carbon atoms; n represents an integer from 1 to 3; plural $R^1$s and plural Xs present in the formula may be respectively identical or different; and two or more of plural Xs represent an organic group having a norbornane epoxy structure.

8 Claims, 1 Drawing Sheet

(56) References Cited

U.S. PATENT DOCUMENTS

| | | | |
|---|---|---|---|
| 7,019,386 B2* | 3/2006 | Ghoshal | C09D 183/06 257/632 |
| 7,534,901 B2* | 5/2009 | Crivello | C07F 7/0874 549/215 |
| 2002/0137870 A1* | 9/2002 | Crivello | C07F 7/1836 528/10 |

FOREIGN PATENT DOCUMENTS

| | | |
|---|---|---|
| JP | 2006-282988 A | 10/2006 |
| JP | 2006-307128 A | 11/2006 |
| JP | 2008-45088 A | 2/2008 |
| JP | 2013-209525 A | 10/2013 |

OTHER PUBLICATIONS

Office Action for corresponding Chinese Application No. 201580017513.6 dated Apr. 28, 2017 with English Translation.

Crivello et al. "Novel Epoxynorbornane Monomers. 2. Cationic Photopolymerization" Macromolecules, 1996, 29(1), 439-445.

Crivello et al. "Novel Epoxynorbornane Monomers. 1. Synthesis and Characterization" Macromolecules, 1996, 29(1), 433-438.

International Search Report for corresponding PCT application No. PCT/JP2015/059119 dated May 12, 2015 and its English language translation.

Written Opinion for corresponding PCT application No. PCT/JP2015/059119 and its English language translation.

* cited by examiner

[Fig. 1]
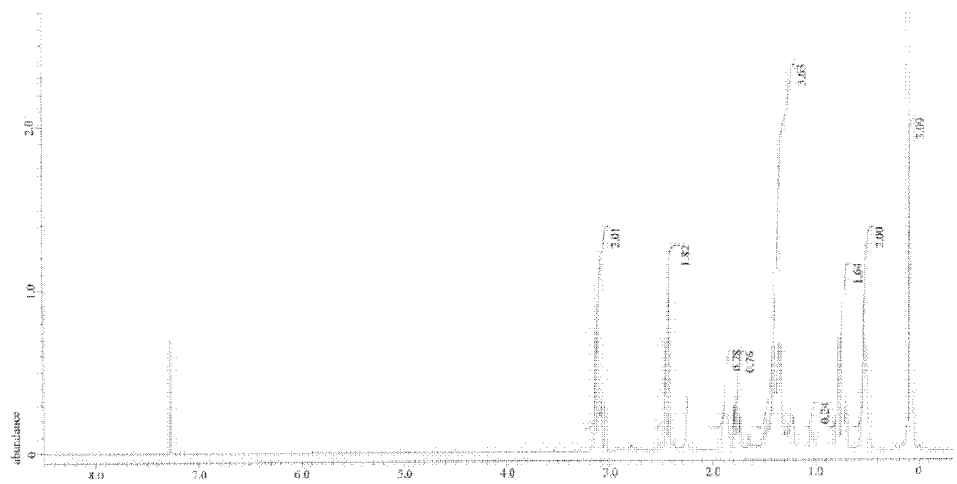
[Fig. 2]
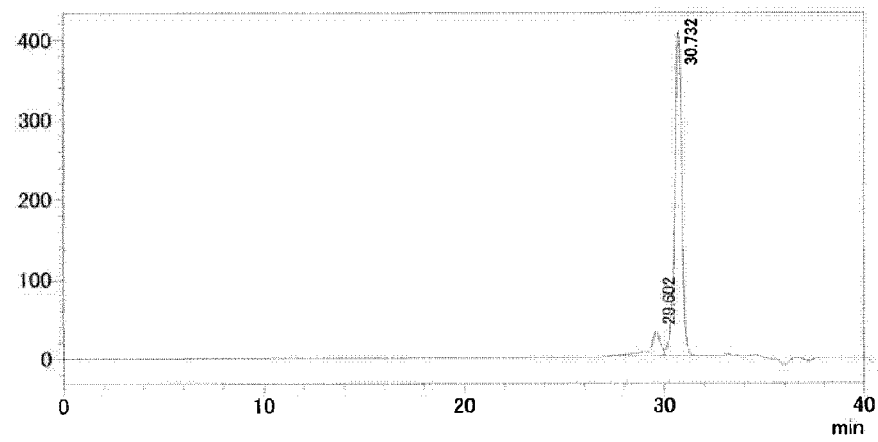

SILICONE-MODIFIED EPOXY RESIN, COMPOSITION CONTAINING THE EPOXY RESIN, AND CURED PRODUCT OF SAME

BACKGROUND ART

Regarding photosemiconductor element sealing resin compositions, compositions each including a bisphenol A type epoxy resin having excellent adhesiveness or mechanical strength, an epoxy resin which has no UV absorption, for example, a hydrogenated bisphenol A type epoxy resin or an alicyclic epoxy resin, a curing agent, and a curing catalyst, have been frequently used. However, along with the increase in the luminance and output power of LED elements, these compositions have problems such as discoloration and cracking, due to the light, heat and the like emitted by LED elements.

As a solution for solving these problems, there is known a resin obtainable by introducing an epoxy group into a silicone resin which yields a cured product that does not absorb UV radiation and has flexibility. For example, a silicone resin having one or more units of a cyclic ether-containing group such as a glycidyl group or an epoxycyclohexyl group (Patent Literature 1); a reaction product of an epoxyalkoxysilane and silanol (Patent Literature 2); and a combination of an alicyclic epoxy-modified silicone resin and an alicyclic epoxy resin (Patent Literature 3) are known. However, since silicone resins have very high gas permeability compared to epoxy resins, as the silicone content increases, it becomes more difficult to use silicone resins in applications where low gas permeability is needed. Thus, an addition reaction type phenyl-based silicone resin composition has been disclosed as a resin composition having low gas permeability (Patent Literature 4); however, even this silicone resin composition is still not satisfactory in the aspects of low gas permeability and adhesiveness.

CITATION LIST

Patent Literature

Patent Literature 1: JP 2008-45088 A
Patent Literature 2: JP 7-97433 A
Patent Literature 3: JP 2006-282988 A
Patent Literature 4: JP 2002-265787 A

SUMMARY OF INVENTION

Technical Problem

The present invention was achieved in view of such circumstances, and it is an object of the invention to provide a silicone-modified epoxy resin composition which yields a cured product having low gas permeability and excellent strength, and an epoxy resin cured product obtainable by curing the relevant composition.

The present inventors conducted a thorough investigation in view of such circumstances as described above, and as a result, the inventors completed the present invention. That is, the present invention relates to the following items (1) to (10).

(1) A silicone-modified epoxy resin (A) represented by the following Formula (1):

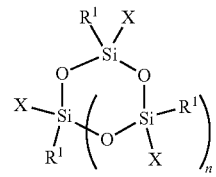

(1)

wherein $R^1$ represents a hydrocarbon group having 1 to 6 carbon atoms; X represents an organic group represented by the following Formula (2) or a hydrocarbon group having 1 to 6 carbon atoms; n represents an integer from 1 to 3; plural $R^1$s and plural Xs present in the formula may be respectively identical or different; and two or more of plural Xs represent an organic group represented by the following Formula (2):

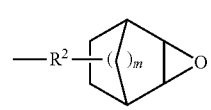

(2)

wherein $R^2$ represents an alkylene group having 2 to 3 carbon atoms; and m represents an integer from 0 to 2.

(2) The silicone-modified epoxy resin according to (1), wherein the silicone-modified epoxy resin is an addition reaction product between a compound represented by the following Formula (3) and a compound represented by the following Formula (4):

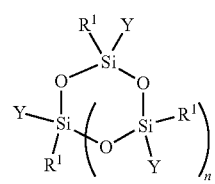

(3)

wherein $R^1$ and n respectively have the same meanings as defined above; each Y represents a hydrogen atom or a hydrocarbon group having 1 to 6 carbon atoms; plural $R^1$s and plural Ys present in Formula may be respectively identical or different; and two or more of plural Ys represent hydrogen atoms:

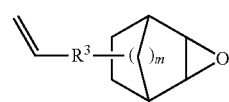

(4)

wherein m has the same meaning as defined above; and $R^3$ represents a single bond or a methylene group.

(3) The silicone-modified epoxy resin according to (1), wherein the silicone-modified epoxy resin is obtained by oxidizing a polyvalent olefin-based compound represented by the following Formula (5):

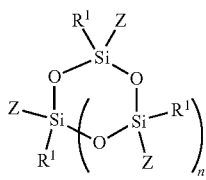

(5)

wherein $R^1$ and n respectively have the same meanings as defined above; Z represents an organic group represented by the following Formula (6) or a hydrocarbon group having 1 to 6 carbon atoms; plural $R^1$s and plural Zs present in Formula may be respectively identical or different; and two or more of plural Zs represent an organic group represented by the following Formula (6):

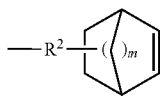

(6)

wherein $R^2$ and m respectively have the same meanings as defined above.

(4) The silicone-modified epoxy resin according to any one of (1) to (3), wherein n is 2.
(5) An epoxy resin composition including the (A) silicone-modified epoxy resin according to any one of (1) to (4); and (B) an epoxy resin curing agent.
(6) An epoxy resin composition including the (A) silicone-modified epoxy resin according to any one of (1) to (4); and (C) an epoxy resin curing accelerator.
(7) An epoxy resin composition, wherein the epoxy resin curing agent according to (5) is at least one selected from amine-based curing agents, phenolic curing agents, acid anhydride-based curing agents, and polyvalent carboxylic acid resins.
(8) A cured product obtained by curing the epoxy resin composition according to any one of (5) to (7).

BRIEF DESCRIPTION OF DRAWINGS

FIG. 1 is the $^1$H-NMR spectrum of a silicone-modified epoxy resin (A-1) obtained in Example 1; and
FIG. 2 is a GPC chart of the silicone-modified epoxy resin (A-1) obtained in Example 1, as analyzed by GPC (B).

DESCRIPTION OF EMBODIMENTS

The present silicone-modified epoxy resin is a cyclic silicone-modified epoxy resin represented by the following Formula (1).

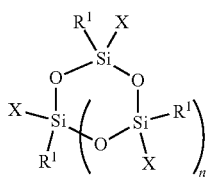

(1)

In Formula (1), $R^1$ represents a hydrocarbon group having 1 to 6 carbon atoms; X represents an organic group represented by the following Formula (2) or a hydrocarbon group having 1 to 6 carbon atoms; n represents an integer from 1 to 3. Plural $R^1$s and plural Xs present in the formula may be respectively identical or different. Two or more of plural Xs represent an organic group represented by the following Formula (2).

$R^1$ represents a hydrocarbon group having 1 to 6 carbon atoms, and specific examples thereof may include, but not limited to, a methyl group, an ethyl group, a propyl group, a butyl group, a pentyl group, a hexyl group, and a phenyl group. However, from the viewpoint of heat-resistant transparency of the cured product, a methyl group and a phenyl group are preferred, and above all, a methyl group is particularly preferred.

X represents an organic group represented by the following Formula (2), or a hydrocarbon group having 1 to 6 carbon atoms, and specific examples of the hydrocarbon group having 1 to 6 carbon atoms may include, but not limited to, a methyl group, an ethyl group, a propyl group, a butyl group, a pentyl group, a hexyl group, and a phenyl group. However, from the viewpoint of heat-resistant transparency of the cured product, a methyl group and a phenyl group are preferred, and above all, a methyl group is particularly preferred.

n represents an integer from 1 to 3, and above all, 2 is preferred.

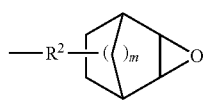

(2)

In Formula (2), $R^2$ represents an alkylene group having 2 or 3 carbon atoms, and above all, from the viewpoint of heat-resistant transparency of the cured product, an ethylene group or a propylene group is preferred.

m represents an integer from 0 to 2, and is preferably 1.

The present silicone-modified epoxy resin may be obtained by subjecting a cyclic hydrogen siloxane compound represented by the following Formula (3) and a compound having an alkenyl group and an epoxy group, which is represented by the following Formula (4), to an addition reaction.

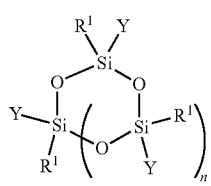

(3)

In Formula (3), $R^1$ and n respectively have the same meanings as defined above; each Y represents a hydrogen atom or a hydrocarbon group having 1 to 6 carbon atoms. Plural $R^1$s and plural Ys present in Formula may be respectively identical or different. Two or more of plural Ys represent hydrogen atoms.

Y represents a hydrogen atom or a hydrocarbon group having 1 to 6 carbon atoms, and specific examples of the hydrocarbon group having 1 to 6 carbon atoms may include, but not limited to, a methyl group, an ethyl group, a propyl group, a butyl group, a pentyl group, a hexyl group, and a phenyl group. However, from the viewpoint of heat-resistant transparency of the cured product, a methyl group or a phenyl group is preferred, and above all, a methyl group is particularly preferred. However, two or more of plural Ys that exist in the compound are hydrogen atoms, and preferably, three or four of Ys are hydrogen atoms.

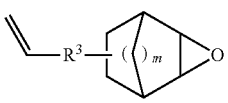

(4)

In Formula (4), m has the same meaning as defined above, and $R^3$ represents a single bond or a methylene group, while, above all, a single bond is preferred.

The compound represented by Formula (4) may be obtained by subjecting a compound represented by the following Formula (7) to oxidative epoxidation.

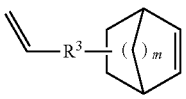

(7)

In Formula (7), m and $R^3$ respectively have the same meanings as defined above.

Examples of the technique for oxidative epoxidation may include, but not limited to, a method of oxidizing a compound using a peracid such as peracetic acid; a method of oxidizing a compound using aqueous hydrogen peroxide; and a method of oxidizing a compound using air (oxygen).

Specific examples of the technique for epoxidation using a peracid may include, but not limited to, the technique described in JP 2006-52187 A. Examples of the peracid that may be used include organic acids such as formic acid, acetic acid, propionic acid, maleic acid, benzoic acid, m-chlorobenzoic acid, and phthalic acid; and acid anhydrides thereof. Among these, from the viewpoints of the efficiency by which the peracid reacts with hydrogen peroxide to produce an organic peracid, the reaction temperature, convenience of the operation, economic efficiency, and the like, it is preferable to use formic acid, acetic acid, or phthalic anhydride, and particularly from the viewpoint of the convenience of the reaction operation, it is more preferable to use formic acid or acetic acid.

In regard to the technique for epoxidation using aqueous hydrogen peroxide, various techniques may be applied. Specifically, the techniques mentioned in JP 59-108793 A, JP 62-234550 A, JP 5-213919 A, JP 11-349579 A, JP 1-33471 B, JP 2001-17864 A, JP 3-57102 B and the like may be applied.

In addition to them, the method described in Non Patent Literature 1 (James V. Crivello and Ramesh Narayan, Novel Epoxynorbornane Monomers. 1. Synthesis and Characterization, Macromolecules, 1996, Vol. 29, pp. 433-438) may also be applied. Specifically, the compound may be obtained by epoxidizing an alkenyl group using oxone.

A preferred method that may be used to obtain the compound represented by Formula (4) is a method in which a compound represented by Formula (7), which is a precursor thereof, a polyacid compound, and a quaternary ammonium salt are allowed to react in two layers between the compound represented by Formula (7) with a monoepoxy compound represented by Formula (4), and aqueous hydrogen peroxide, in an organic solvent or without solvent.

The polyacid compound used for the oxidative epoxidation is not particularly limited as long as it is a compound having a polyacid structure; however, a polyacid compound containing tungsten or molybdenum is preferred; a polyacid compound containing tungsten is more preferred; and a tungstic acid salt is particularly preferred.

Specific examples of the polyacid and polyacid salts that are included in the polyacid class may include, but not limited to, a tungsten-based acid selected from tungstic acid, 12-tungstophosphoric acid, 12-tungstoboric acid, 18-tungstophosphoric acid, and 12-tungstosilicic acid; a molybdenum-based acid selected from molybdic acid and phosphomolybdic acid; and salts thereof.

Examples of the counter cations for these salts may include, but not limited to, ammonium ion, an alkaline earth metal ion, and an alkali metal ion.

Specific examples may include, but not limited to, alkaline earth metal ions such as calcium ion and magnesium ion; and alkali metal ions such as sodium, potassium, and cesium ions. Particularly preferred examples of the counter cations may include, but not limited to, sodium ion, potassium ion, calcium ion, and ammonium ion.

The amount of use of the polyacid compound is, in terms of the metal element (number of moles of tungsten atoms constituting tungstic acid or molybdenum atoms constituting molybdic acid), 1.0 to 40 mmol, preferably 2.0 to 30 mmol, and more preferably 2.5 to 25 mmol, relative to 1 mol of alkenyl groups (functional group equivalent) in the olefin-based compound.

Regarding the quaternary ammonium salt, a quaternary ammonium salt having a total number of carbon atoms of 10 or greater, preferably 25 to 100, and more preferably 25 to 55, may be preferably used, and particularly, a quaternary ammonium salt in which the alkyl chains are all aliphatic chains, is preferred.

Specific examples may include, but not limited to, a tridecanylmethylammonium salt, a dilauryldimethylammonium salt, a trioctylmethylammonium salt, a trialkylmethyl (a mixed type of a compound in which the alkyl group is an octyl group and a compound in which the alkyl group is a decanyl group)ammonium salt, a trihexadecylmethylammonium salt, a trimethylstearylammonium salt, a tetrapentylammonium salt, a cetyltrimethylammonium salt, a benzyltributylammonium salt, a dicetyldimethylammonium salt, a tricetylmethylammonium salt, and a di-hardened tallow alkyldimethylammonium salt.

Furthermore, regarding the anion species for these salts, a carboxylate ion is used. Regarding the carboxylate ion, acetate ion, carbonate ion, and formate ion are preferred. Furthermore, acetate ion is particularly preferred.

If the number of carbon atoms of the quaternary ammonium salt is more than 100, hydrophobicity becomes too strong, and solubility of the ammonium salt in the organic layer may become poor. On the other hand, if the number of carbon atoms of the quaternary ammonium salt is less than 10, hydrophilicity becomes strong, and similarly, compatibility with the organic layer may become poor.

Quaternary ammonium salts generally include residual halogen atoms. According to the present invention, the amount of halogen is particularly 1% by mass or less, more preferably 1,000 ppm or less, and even more preferably 700 ppm or less. In a case in which the total amount of halogen is more than 1% by mass, it is not preferable because a large amount of halogen remains in the product.

The amounts of use of the tungstic acid compound and the quaternary ammonium carboxylic acid salt are preferably 0.01 to 0.8 times equivalent or 1.1 to 10 times equivalent of the valence of the tungstic acid compound used. The amounts of use are more preferably 0.05 to 0.7 times equivalent or 1.2 to 6.0 times equivalent, even more preferably 0.05 to 0.5 times equivalent or 1.3 to 4.5 times equivalent.

For example, since tungstic acid is $H_2WO_4$ and is divalent, the amount of use of the quaternary ammonium carboxylate is preferably in the range of 0.02 to 1.6 mol or 2.2 to 20 mol, relative to 1 mol of tungstic acid. Furthermore, since tungstophosphoric acid is trivalent, similarly, the amount of use is preferably 0.03 to 2.4 mol or 3.3 to 30 mol, and since silicotungstic acid is tetravalent, the amount of use is preferably 0.04 to 3.2 mol or 4.4 to 40 mol.

In a case in which the amount of the quaternary ammonium carboxylate is lower than 1.1 times equivalent of the valence of the tungstic acid compound, it is difficult for the epoxidation reaction to proceed (in some cases, the progress of the reaction is rapid), and there is a problem that side products may be easily produced. In a case in which the amount of the quaternary ammonium carboxylate is larger than 10 times equivalent, not only the treatment of an excess of the quaternary ammonium carboxylate is difficult, but also the carboxylate has a function of suppressing the reaction, which is not preferable.

Regarding the quaternary ammonium salt that uses carboxylate ion as the anion, a commercially available product may be used, and may also be produced by, for example, a method of treating a raw material quaternary ammonium salt with a metal hydroxide or an ion exchange resin, converting the raw material quaternary ammonium salt into quaternary ammonium hydroxide, and reacting the quaternary ammonium hydroxide with various carboxylic acids. Examples of the raw material quaternary ammonium salt include halides or various metal salts of quaternary ammoniums. Furthermore, if a suitable quaternary ammonium hydroxide is available, this may also be used.

Any kind of buffer solution may all be used; however, it is preferable to use an aqueous phosphate solution for the present reaction. The pH of the buffer solution is preferably adjusted to be between pH 2 and 10, and more preferably between pH 3 and 9. In the case of a pH below 2, a hydrolysis reaction and a polymerization reaction of epoxy groups may proceed easily. Furthermore, in the case of a pH above 10, the reactions are extremely prolonged, and there occurs a problem that the reaction time becomes too long.

Particularly, according to the present invention, it is preferable that the buffer solution is adjusted to be between pH 2 and 9 when a tungstic acid compound as a catalyst is dissolved therein.

An example of the method for using a buffer solution may be a method of using, in the case of an aqueous solution of phosphoric acid-phosphate as a preferable buffer solution, 0.1 mol % equivalent to 10 mol % equivalent of phosphoric acid (or a phosphate such as sodium dihydrogen phosphate) with respect to hydrogen peroxide, and performing pH adjustment with a basic compound (for example, sodium hydroxide, potassium hydroxide, sodium carbonate, sodium hydrogen carbonate, or potassium carbonate). Here, regarding the pH, it is preferable to add the basic compound such that the pH described above is obtained when hydrogen peroxide is added. Furthermore, the pH may also be adjusted using sodium dihydrogen phosphate, disodium hydrogen phosphate or the like. A preferred concentration of the phosphate is 0.1% to 60% by mass, and preferably 5% to 45% by mass.

Furthermore, for the present reaction, a phosphate such as disodium hydrogen phosphate, sodium dihydrogen phosphate, sodium phosphate, or sodium tripolyphosphate (or a hydride thereof) may be added directly without using a buffer solution and without pH adjustment. In view of simplification of the process, direct addition is particularly preferred because there is no need to bother about pH adjustment. The amount of use of the phosphate in this case is usually 0.1 mol % equivalent to 5 mol % equivalent, preferably 0.2 mol % equivalent to 4 mol % equivalent, and more preferably 0.3 mol % equivalent to 3 mol % equivalent, with respect to hydrogen peroxide. At this time, if the amount of use is more than 5 mol % equivalent with respect to hydrogen peroxide, pH adjustment is needed, and in a case in which the amount of use is less than 0.1 mol % equivalent, there may be disadvantages such as that a hydrolysis product of the epoxy resin thus produced is easily produced, or the reaction is prolonged.

Regarding the hydrogen peroxide used for the present reaction, an aqueous solution having a hydrogen peroxide concentration of 10% to 40% by mass is preferred from the viewpoint of the convenience of handling thereof. In a case in which the concentration is more than 40% by mass, handling becomes difficult, and the decomposition reaction of the epoxy resin thus produced also easily occurs, which is not preferable.

In the present reaction, an organic solvent may be used. The amount of the organic solvent in the case of using one is, as a mass ratio, 0.3 to 10, preferably 0.3 to 5, and more preferably 0.5 to 2.5, relative to 1 of the olefin-based compound as a reaction substrate. In a case in which the amount of the organic solvent is more than 10 as a mass ratio, it is not preferable because the progress of the reaction is extremely delayed. Specific examples of the organic solvent that may be used may include, but not limited to, alkanes such as hexane, cyclohexane, and heptane; aromatic hydrocarbon compounds such as toluene and xylene; and alcohols such as methanol, ethanol, isopropanol, butanol, hexanol, and cyclohexanol. Furthermore, depending on the cases, ketones such as methyl ethyl ketone, methyl isobutyl ketone, cyclopentanone, and anone; ethers such as diethyl ether, tetrahydrofuran, and dioxane; ester compounds such as ethyl acetate, butyl acetate, and methyl formate; and nitrile compounds such as acetonitrile, may also be used.

Regarding a specific reaction operation method, for example, when the reaction is carried out in a batch type reaction pot, an olefin-based compound, hydrogen peroxide (aqueous solution), a polyacid compound (catalyst), a buffer solution, a quaternary ammonium salt, and an organic solvent are mixed and stirred in two layers. The stirring speed is not particularly defined. Since heat generation frequently occurs at the time of adding hydrogen peroxide, a method of slowly adding hydrogen peroxide after adding various components may also be used.

The reaction temperature is not particularly limited; however, the reaction temperature is preferably 0° C. to 90° C., more preferably 0° C. to 75° C., and particularly preferably 15° C. to 60° C. In a case in which the reaction temperature is too high, a hydrolysis reaction easily proceeds, and if the reaction temperature is low, the reaction rate is extremely slowed.

Furthermore, the reaction time may vary depending on the reaction temperature, the amount of catalyst, or the like; however, from the viewpoint of industrial production, a reaction for a long time is not preferable because enormous energy should be consumed. A preferred range of the reaction time is 1 to 48 hours, preferably 3 to 36 hours, and more preferably 4 to 24 hours.

After completion of the reaction, a quench treatment of excess hydrogen peroxide is performed. It is preferable to perform the quench treatment using a basic compound. Furthermore, it is also preferable to use a reducing agent and a basic compound in combination. A preferred example of the treatment method may be a method of neutralizing and adjusting the pH to 6 to 12 with a basic compound, and then quenching residual hydrogen peroxide using a reducing agent. In a case in which the pH is below 6, heat generation occurs significantly when excess hydrogen peroxide is reduced, and there is a possibility that a decomposition product may be produced.

Examples of the reducing agent may include, but not limited to, sodium sulfite, sodium thiosulfate, hydrazine, oxalic acid, and vitamin C. The amount of use of the reducing agent is usually 0.01 to 20 molar times, more preferably 0.05 to 10 molar times, and even more preferably 0.05 to 3 molar times, relative to the number of moles of excess hydrogen peroxide.

Examples of the basic compound include metal hydroxides such as sodium hydroxide, potassium hydroxide, magnesium hydroxide, and calcium hydroxide; metal carbonates such as sodium carbonate and potassium carbonate; phosphates such as sodium phosphate and sodium hydrogen phosphate; and basic solids such as an ion exchange resin and alumina.

Regarding the amount of use thereof, as long as the basic compound dissolves in water or organic solvents (for example, various solvents such as aromatic hydrocarbons such as toluene and xylene; ketones such as methyl isobutyl ketone and methyl ethyl ketone; hydrocarbons such as cyclohexane, heptane and octane; and alcohols such as methanol, ethanol and isopropyl alcohol), the amount of use thereof is usually 0.01 to 20 molar times, more preferably 0.05 to 10 molar times, and even more preferably 0.05 to 3 molar times, relative to the number of moles of excess hydrogen peroxide. These may be added as solutions in water or the organic solvents described above, or may also be added as simple substances.

In a case in which a solid base that does not dissolve in water or an organic solvent is used, it is preferable to use the solid base in an amount of 1 to 1000 times as a mass ratio with respect to the amount of hydrogen peroxide remaining in the system. It is more preferable to use the solid base in an amount of 10 to 500 times, and even more preferably 10 to 300 times. In a case in which a solid base that does not dissolve in water or an organic solvent is used, the treatment may be carried out after the separation of an aqueous layer and an organic layer that will be described below.

After quenching of hydrogen peroxide (or before performing quench), at this time, in a case in which an organic layer and an aqueous layer are not separated, or an organic solvent is not used, the operation is carried out by adding the organic solvent described above, and extraction of the reaction product from the aqueous layer is performed. The amount of the organic solvent used at this time is 0.5 to 10 times, and preferably 0.5 to 5 times, as a mass ratio with respect to the raw material olefin-based compound. This operation is repeated several times as necessary, subsequently the organic layer is separated, and the organic layer is washed with water and purified if necessary.

The organic layer thus obtained is subjected to removal of impurities, if necessary, using an ion exchange resin or a metal oxide (particularly, silica gel, alumina or the like is preferred), activated carbon (above all, chemically activated carbon is particularly preferred), a composite metal salt (above all, a basic composite metal salt is particularly preferred), a clay mineral (above all, a layered clay mineral such as montmorillonite is particularly preferred), or the like. The organic layer is further subjected to washing with water, filtration and the like, and then the solvent is distilled off. Thus, an intended epoxy compound is obtained. Depending on cases, the epoxy compound may be further purified by column chromatography or distillation.

At the time of oxidative epoxidation of the compound represented by Formula (7), depending on the reaction conditions, the compound represented by Formula (4) described above and a compound represented by the following Formula (8) may be produced as a mixture.

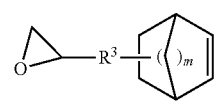

(8)

In Formula (8), m and $R^3$ respectively have the same meanings as defined above.

In a case in which the compound represented by Formula (1) of the present invention is obtained by an addition reaction between the compound represented by Formula (3) and the compound represented by Formula (4), the compound represented by Formula (4) may be supplied as a mixture with the compound represented by Formula (8).

In a case in which the compound represented by Formula (4) is mixed with the compound represented by Formula (8), the proportion of the compound represented by Formula (8) is preferably 15% by mass or less, and more preferably 10% by mass or less, in the mixture. If the compound is included in an amount greater than 15% by mass, there is a possibility that the cured product may have inferior heat-resistant transparency.

With regard to the addition reaction between the compound represented by Formula (3) and the compound represented by Formula (4) (in the case of mixing, the compound represented by Formula (8)), the product may be produced by a hydrosilylation reaction in the presence of a platinum catalyst.

The present silicone-modified epoxy resin may also be obtained by oxidizing an olefin-based compound represented by the following Formula (5), which is a precursor of the epoxy resin.

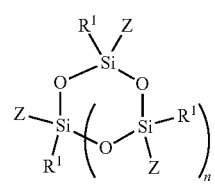

(5)

In Formula (5), $R^1$ and n respectively have the same meanings as defined above; Z represents an organic group represented by the following Formula (6) or a hydrocarbon group having 1 to 6 carbon atoms. Plural $R^1$s and plural Zs present in Formula may be respectively identical or different. Two or more of plural Zs represent an organic group represented by the following Formula (6)

In Formula (5), Z represents an organic group represented by the following Formula (6) or a hydrocarbon group having 1 to 6 carbon atoms, and specific examples of the hydrocarbon group having 1 to 6 carbon atoms may include, but not limited to, a methyl group, an ethyl group, a propyl group, a butyl group, a pentyl group, a hexyl group, and a phenyl group. However, from the viewpoint of heat-resistant transparency of the cured product, a methyl group and a phenyl group are preferred, and above all, a methyl group is particularly preferred.

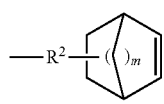
(6)

In Formula (6), $R^2$ and m respectively have the same meanings as defined above.

Regarding the technique for oxidation, oxidation may be carried out by a method similar to the oxidative epoxidation method described above as an example.

The epoxy equivalent of the present silicone-modified epoxy resin obtainable as such is preferably 150 to 450 g/eq., more preferably 160 to 300 g/eq., and even more preferably 180 to 250 g/eq. In a case in which the epoxy equivalent is less than 150 g/eq., the cured product tends to become too hard, and in a case in which the epoxy equivalent is more than 450 g/eq., the mechanical characteristics of the cured product tend to be deteriorated, which is not preferable. Also, it is preferable that the silicone-modified epoxy resin is liquid.

The epoxy equivalent may be determined by the method described in JIS K7236, or from $^1$H-NMR, $^{13}$C-NMR, $^{29}$Si-NMR, elemental analysis, or the like.

The present epoxy resin composition includes (A) a silicone-modified epoxy resin, and (B) an epoxy resin curing agent.

Here, the (B) epoxy resin curing agent will be explained.

As the (B) epoxy resin curing agent, a curing agent having a functional group that is reactive with an epoxy group is used. Examples thereof may include, but not limited to, an amine-based curing agent, a phenolic curing agent, an acid anhydride-based curing agent, and a polyvalent carboxylic acid resin, and among them, an acid anhydride-based curing agent and a polyvalent carboxylic acid resin are preferred. Examples of the acid anhydride-based curing agent may include, but not limited to, phthalic anhydride, maleic anhydride, trimellitic anhydride, pyromellitic anhydride, hexahydrophthalic anhydride, 3-methylhexahydrophthalic anhydride, 4-methylhexahydrophthalic anhydride, a mixture of 3-methylhexahydrophthalic anhydride and 4-methylhexahydrophthalic anhydride, tetrahydrophthalic anhydride, nadic anhydride, methyl nadic anhydride, norbornane-2,3-dicarboxylic acid anhydride, methylnorbornane-2,3-dicarboxylic acid anhydride, and 2,4-diethylglutaric anhydride. Among these, hexahydrophthalic anhydride and derivatives thereof are preferred.

Next, the polyvalent carboxylic acid resin will be explained.

A polyvalent carboxylic acid resin is a compound which has at least two or more carboxyl groups and has an aliphatic hydrocarbon group or a siloxane skeleton as a main skeleton. According to the present invention, the polyvalent carboxylic acid resin includes not only a polyvalent carboxylic acid compound having a single structure, but also a mixture of plural compounds having different positions of substituents or different substituents, that is, a polyvalent carboxylic acid composition, and in the present invention, those are collectively referred to as polyvalent carboxylic acid resins.

The polyvalent carboxylic acid resin is particularly preferably a bifunctional to hexafunctional carboxylic acid, and a compound obtained by a reaction between a bifunctional to hexafunctional polyhydric alcohol having 5 or more carbon atoms or a polyhydric alcohol having a siloxane structure and an acid anhydride, is more preferred. Furthermore, a polycarboxylic acid in which the above-mentioned acid anhydride is a saturated aliphatic cyclic acid anhydride is preferred.

Regarding the bifunctional to hexafunctional polyhydric alcohol, as an alcohol compound, a compound having alcoholic hydroxyl groups is not particularly limited, and examples thereof may include diols such as ethylene glycol, propylene glycol, 1,3-propanediol, 1,2-butanediol, 1,4-butanediol, 1,5-pentanediol, 1,6-hexanediol, cyclohexanedimethanol, 2,4-diethylpentanediol, 2-ethyl-2-butyl-1,3-propanediol, neopentyl glycol, tricyclodecanedimethanol, and norbornenediol; triols such as glycerin, trimethylolethane, trimethylolpropane, trimethylolbutane, and 2-hydroxymethyl-1,4-butanediol; tetraols such as pentaerythritol and ditrimethylolpropane; and hexaols such as dipentaerythritol.

A particularly preferred alcohol compound is an alcohol having 5 or more carbon atoms, and in particular, compounds such as 1,6-hexanediol, 1,4-cyclohexanedimethanol, 1,3-cyclohexanedimethanol, 1,2-cyclohexanedimethanol, 2,4-diethylpentanediol, 2-ethyl-2-butyl-1,3-propanediol, neopentyl glycol, tricyclodecanedimethanol, and norbornenediol may be mentioned. Among them, alcohol compounds having a branched structure or cyclic structure, such as 2-ethyl-2-butyl-1,3-propanediol, neopentyl glycol, 2,4-diethylpentanediol, 1,4-cyclohexanedimethanol, tricyclodecanedimethanol, and norbornenediol, are more preferred. From the viewpoint of imparting a high illuminance retention ratio, 2,4-diethylpentanediol and tricyclodecanedimethanol are particularly preferred.

The polyhydric alcohol having a siloxane structure is not particularly limited; however, for example, a silicone oil represented by the following Formula (9) may be used.

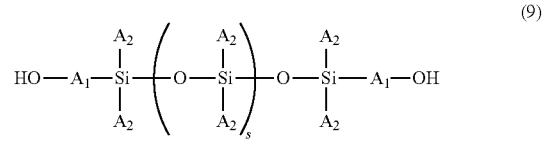
(9)

In Formula (9), $A_1$ represents an alkylene group having 1 to 10 carbon atoms in total, which may be interrupted by an ether bond, and $A_2$ represents a methyl group or a phenyl group. Furthermore, s represents a number of repetitions, and means an average value ranging from 1 to 100.

Particularly preferred examples of the acid anhydride may include, but not limited to, methyltetrahydrophthalic anhydride, methyl nadic anhydride, nadic anhydride, hexahydrophthalic anhydride, methylhexahydrophthalic anhydride, butanetetracarboxylic acid anhydride, bicyclo[2,2,1]heptane-2,3-dicarboxylic acid anhydride, methylbicyclo[2,2,1]heptane-2,3-dicarboxylic acid anhydride, and cyclohexane-1,3,4-tricarboxylic acid-3,4-anhydride, and among them, methylhexahydrophthalic anhydride and cyclohexane-1,3,4- tricarboxylic acid-3,4-anhydride are preferred. Here, in order to increase hardness, cyclohexane-1,3,4-tricarboxylic acid-3,4-anhydride is preferred, and in order to increase illuminance retention ratio, methylhexahydrophthalic anhydride is preferred.

The conditions for the addition reaction are not particularly limited; however, one of specific reaction conditions is a technique by which an acid anhydride and a polyhydric alcohol are reacted at 40° C. to 150° C. under catalyst-free and solvent-free conditions to be heated, and after completion of the reaction, the reaction product is taken out as it is. However, the present invention is not intended to be limited to the present reaction conditions.

The polyvalent carboxylic acid resin obtainable in this manner is particularly preferably a compound represented by the following Formula (10).

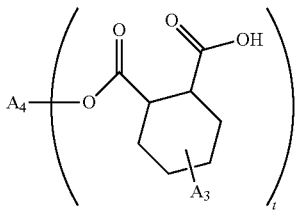

(10)

In Formula (10), $A_3$, which is present as plural units, represents at least one of a hydrogen atom, a methyl group, and a carboxyl group. $A_4$ represents a chain-like or cyclic aliphatic group having 2 to 20 carbon atoms, which is derived from one of the polyhydric alcohols described above, and/or an alkylene group having 1 to 10 carbon atoms in total, which has a siloxane structure derived from a polyhydric alcohol having a siloxane structure, and may be interrupted by an ether bond. t represents an integer from 2 to 4.

It is preferable that the (B) epoxy resin curing agent according to the present invention includes an acid anhydride. Specific examples of the acid anhydride may include, but not limited to, acid anhydrides such as phthalic anhydride, trimellitic anhydride, pyromellitic anhydride, maleic anhydride, tetrahydrophthalic anhydride, methyltetrahydrophthalic anhydride, methyl nadic anhydride, nadic anhydride, hexahydrophthalic anhydride, methylhexahydrophthalic anhydride, butanetetracarboxylic acid dihydride, bicyclo[2,2,1]heptane-2,3-dicarboxylic acid anhydride, methylbicyclo[2,2,1]heptane-2,3-dicarboxylic acid anhydride, and cyclohexane-1,3,4-tricarboxylic acid-3,4-anhydride.

Especially, preferred examples may include, but not limited to, methyltetrahydrophthalic anhydride, methyl nadic anhydride, nadic anhydride, hexahydrophthalic anhydride, methylhexahydrophthalic anhydride, butanetetracarboxylic acid anhydride, bicyclo[2,2,1]heptane-2,3-dicarboxylic acid anhydride, methylbicyclo[2,2,1]heptane-2,3-dicarboxylic acid anhydride, and cyclohexane-1,3,4-tricarboxylic acid-3,4-anhydride.

Particularly preferred examples may include, but not limited to, a hexahydrophthalic anhydride represented by the following Formula (11), methylhexahydrophthalic anhydride, and cyclohexane-1,3,4-tricarboxylic acid-3,4-anhydride, and among them, methylhexahydrophthalic anhydride and cyclohexane-1,3,4-tricarboxylic acid-3,4-anhydride are preferred.

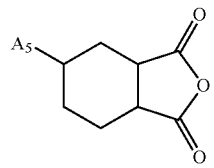

(11)

In Formula (11), $A_5$ represents at least one or more of a hydrogen atom, a methyl group, and a carboxyl group.

It is preferable to use a polyvalent carboxylic acid resin and an acid anhydride in combination, and in the case of using the compounds in combination, the use ratio is preferably in the range described below.

$$W1/(W1+W2)=0.05 \text{ to } 0.70$$

provided that W1 represents the parts by mass of a polyvalent carboxylic acid resin incorporated, and W2 represents the parts by mass of an acid anhydride. The range of W1/(W1+W2) is more preferably 0.05 to 0.60, even more preferably 0.10 to 0.55, and particularly preferably 0.15 to 0.4. If the ratio is less than 0.05, there is a strong tendency that volatilization of the acid anhydride occurs to a large extent at the time of curing, and it is not preferable. If the ratio is more than 0.70, the viscosity becomes high, and handling is made difficult. In a case in which an acid anhydride is not incorporated (excluding the case in which a small amount of an acid anhydride remains), the shape of the acid anhydride is solid or in a state close to solid, or the acid anhydride becomes crystals, and there is no problem.

In a case in which a polyvalent carboxylic acid resin and an acid anhydride are used in combination, a technique of producing the polyvalent carboxylic acid resin in an excess of the acid anhydride at the time of producing the polyvalent carboxylic acid resin, and obtaining a mixture of the polyvalent carboxylic acid and the acid anhydride, is also preferable from the viewpoint of convenience of the operation.

The amount of incorporation of the (B) epoxy resin curing agent in the present epoxy resin composition is an amount which provides 0.3 to 1.0 mol, preferably 0.4 to 0.8 mol, of the functional group that is reactive with an epoxy group (in the case of an acid anhydride-based curing agent, an acid anhydride group represented by the formula: —CO—O—CO—), relative to 1 mole in total of the epoxy groups in the (A) silicone-modified epoxy resin. When the amount of the functional group that is reactive with an epoxy group is 0.3 mol or more, heat resistance and transparency of the cured product are enhanced, and therefore, it is desirable. When the amount of the functional group is 1.0 mol or less, mechanical characteristics of the cured product are enhanced, and therefore, it is preferable. Here, the "functional group that is reactive with an epoxy group" refers to an amino group contained in an amine-based curing agent, a phenolic hydroxyl group contained in a phenolic curing agent, an acid anhydride group contained in an acid anhydride-based curing agent, or a carboxyl group contained in a polyvalent carboxylic acid resin.

The present epoxy resin composition includes (A) a silicone-modified epoxy resin, and (C) an epoxy resin curing accelerator.

Here, the (C) epoxy resin curing accelerator will be explained.

Examples of the (C) epoxy resin curing accelerator may include, but not limited to, quaternary phosphonium salts such as tetrabutylphosphonium O,O-diethylphosphorodithioate and tetraphenylphosphonium tetraphenylborate; organic phosphine-based curing catalysts such as triphenylphosphine and diphenylphosphine; tertiary amine-based curing catalysts such as 1,8-diazabicyclo(5,4,0)undecene-7, triethanolamine, and benzyldimethylamine; quaternary ammonium salts such as 1,8-diazabicyclo(5,4,0)undecene-7 phenol salt, 1,8-diazabicyclo(5,4,0)undecene-7 octoate, 1,8-diazabicyclo(5,4,0)undecene-7 p-toluenesulfonate, and 1,8-diazabicyclo(5,4,0)undecene-7 formate; organic carboxylic acid salts such as zinc octoate and zinc naphthoate; aluminum chelate compounds such as aluminum bisethylacetoacetate/monoacetylacetonate and aluminum ethyl acetate/diisopropylate; imidazoles such as 2-methylimidazole and 2-phenyl-4-methylimidazole; thermal cation curing accelerators such as aromatic sulfonium salts, aromatic iodonium salts, and antimony-based sulfonium salts; and photocation curing accelerators such as antimony-based sulfonium salts and phosphorus-based sulfonium salts.

The amount of incorporation of the (C) epoxy resin curing accelerator is 0.01 to 3 parts by mass, and preferably 0.05 to 1.5 parts by mass, relative to 100 parts by mass of the sum of component (A) and component (B). If the amount of incorporation of the epoxy resin curing accelerator is smaller than the lower limit, there is a risk that the effect of accelerating the reaction between the epoxy resin and the curing agent may not be sufficient. On the other hand, if the amount of incorporation of the epoxy resin curing accelerator is larger than the upper limit, there is a risk that the epoxy resin curing agent may cause discoloration at the time of curing or at the time of a reflow test.

The present epoxy resin composition may have an oxidation inhibitor added thereto for the purpose of maintaining transparency of the cured product. Examples of the oxidation inhibitor include a phosphorous acid compound and a hindered phenolic oxidation inhibitor, and a hindered phenolic oxidation inhibitor is preferred. Furthermore, regarding an ultraviolet absorbing agent, a hindered amine-based ultraviolet absorbing agent is preferred. The amount of incorporation of the oxidation inhibitor is 0.1 to 0.5 parts by mass, and preferably 0.1 to 0.3 parts by mass, relative to 100 parts by mass of component (A). If the amount of incorporation of the oxidation inhibitor is more than the upper limit, residual oxidation inhibitor is precipitated on the surface of the resin after curing, and therefore, it is not preferable. If the amount of incorporation is less than the lower limit, heat resistance and transparency are deteriorated.

<Other Components>

In addition to the various components described above, conventionally used additives, for example, an ultraviolet absorbing agent, a deterioration inhibitor, a fluorescent material, a thermal plasticizer and a diluent, may be used in combination as necessary.

The present epoxy resin composition may be produced by blending the various components described above and various additives as necessary, and dissolving or melt mixing the components. Melt mixing may be carried out by a known method, and for example, the components described above may be introduced into a reactor and melt mixed in a batch manner, or the various components described above may be introduced into a kneading machine such as a kneader or a hot three-roll and melt mixed continuously. It is preferable that the (C) epoxy resin curing accelerator is heated and dissolved in advance in the (B) epoxy resin curing agent to be mixed, and at the final stage of mixing, the mixture is dispersed and mixed with the (A) silicone-modified epoxy resin component and the like.

EXAMPLES

Hereinafter, the present invention will be described in more detail by way of Synthesis Examples and Examples. Furthermore, the present invention is not intended to be limited to these Synthesis Examples and Examples. Meanwhile, the various physical property values in the Synthesis Examples and Examples were measured by the following methods. Here, the unit "parts" represents parts by mass, unless particularly stated otherwise.

○ GC analysis:
Manufacturer: Shimadzu Corp.
Model: GC2010
Column: HP-5MS manufactured by Agilent Technology, Inc., 15 m
Carrier gas: Helium 1.0 ml/min
Detector: FID
Split ratio: 30:1
Temperature Conditions
Injection: 300° C.
Column: Maintained for 2 minutes at 50° C., temperature increased to 300° C. at 10° C./min, and maintained for 20 minutes at 300° C.
Detector: 300° C.

○ GPC (A): GPC (A) was analyzed under the conditions described below.
Manufacturer: Waters Corp.
Column: SHODEX GPC LF-G (guard column), KF-603, KF-602.5, KF-602, KF-601 (two units)
Flow rate: 0.4 ml/min
Column temperature: 40° C.
Solvent used: THF (tetrahydrofuran)
Detector: RI (differential refractometer)

○ GPC (B): GPC (B) was analyzed under the conditions described below.
Manufacturer: Shimadzu Corp.
Column: SHODEX GPC LF-G (guard column), LF-804 (three units)
Flow rate: 1.0 ml/min
Column temperature: 40° C.
Solvent used: THF (tetrahydrofuran)
Detector: RI (differential refractometer)

○ NMR: Analyzed using JNM-ECS400 manufactured by JEOL, Ltd., and using deuterated chloroform solvent.

[Synthesis Example 1] Synthesis of 5-vinyl-2,3-epoxynorbornane

Into a glass flask equipped with a stirring apparatus and a reflux cooling tube, 240.4 g of 5-vinylnorbornene, 3.64 g of a 50 mass % xylene solution of trioctylmethylammonium acetate (manufactured by Lion Akzo Co., Ltd., TOMAA-50), 40.2 g of water, 5.8 g of phosphotungstic acid n-hydrate, 4.0 g of sodium tungstate dihydrate, and 6.4 g of sodium dihydrogen phosphate dihydrate were introduced, and the mixture was heated to 50±3° C. While the mixture was stirred, 97.2 g of a 35 mass % aqueous solution of hydrogen peroxide was added dropwise thereto for 50 minutes, and the mixture was stirred in that state at 50±3° C. for 9 hours.

The progress of the reaction was checked by $^1$H-NMR, and the conversion ratio of the norbornene-derived intracyclic alkenyl group was 82%.

Subsequently, the mixture was adjusted to pH 9 using a 30% aqueous solution of sodium hydroxide, and then 36 g of a 20% aqueous solution of sodium thiosulfate was added thereto. The mixture was stirred for 30 minutes and then was left to stand. The mixture was separated into two layers, and an organic layer was removed and purified by a vacuum distillation purification method. Thus, 140.1 g of a mixture of 5-vinyl-2,3-epoxynorbornane and 5-glycidylnorbornene was obtained. The GC area ratio of the mixture thus obtained was such that 5-vinyl-2,3-epoxynorbornane occupied 95.4%, and 5-glycidylnorbornene occupied 4.6%.

Example 1

The mixture of 5-vinyl-2,3-epoxynorbornane and 5-glycidylnorbornene (1 mol, 136.2 g) obtained in Synthesis Example 1, 0.18 g of a 0.5 mass % toluene solution of chloroplatinic acid, and 20 g of toluene were introduced into a 1-L separable flask, and the mixture was stirred. Subsequently, the internal temperature was increased to 80° C. Subsequently, 2,4,6,8-tetramethylcyclotetrasiloxane (0.17 mol, 40.09 g) was added dropwise thereto for 1 hour, and the mixture was allowed to react for 4 hours at 110° C. The toluene solution thus obtained was distilled off under reduced pressure, and thus silicone-modified epoxy resin (A-1) that contained the compound (12) described below as a main component was obtained. The $^1$H-NMR spectrum is shown in FIG. 1, and a GPC chart measured by GPC (B) is presented in FIG. 2.

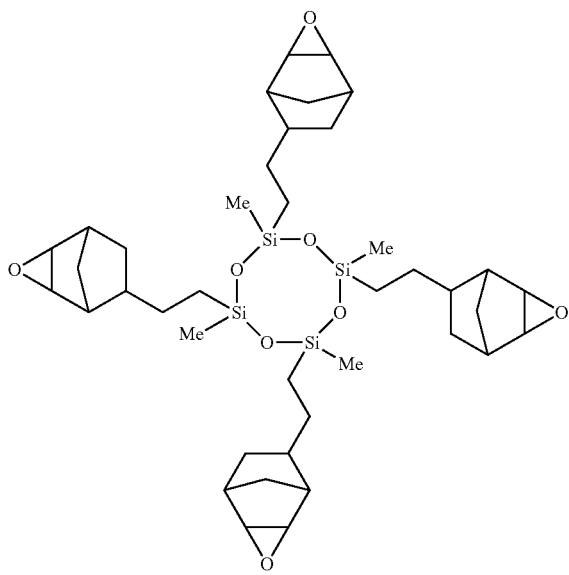

(12)

Synthesis Example 2

[Synthesis of Mixture of Polyvalent Carboxylic Acid Resin and Acid Anhydride Compound Used as Curing Agent]

While a flask equipped with a stirrer, a reflux cooling tube, and a stirring apparatus was purged with nitrogen, 15 g of tricyclodecanedimethanol, 70 g of methylhexahydrophthalic anhydride (manufactured by New Japan Chemical Co., Ltd., RIKACID MH; hereinafter, referred to as acid anhydride H3), and 15 g of cyclohexane-1,2,4-tricarboxylic acid-1,2-anhydride (H-TMAn manufactured by Mitsubishi Gas Chemical Co., Inc.) were introduced into the flask. The mixture was allowed to react for 3 hours at 40° C., and then was subjected to heating and stirring for 1 hour at 70° C. It was checked by GPC that the peak area of tricyclodecanedimethanol was 1% by area or less. Thus, 100 g of a mixture (B-1) of a polyvalent carboxylic acid resin and a carboxylic acid anhydride compound was obtained. The mixture thus obtained was a colorless liquid resin, and the purity determined by GPC (A) was such that the polyvalent carboxylic acid resin (the following Formula (13)) occupied 37% by area, cyclohexane-1,2,4-tricarboxylic acid-1,2-anhydride occupied 11% by area, and methylhexahydrophthalic anhydride occupied 52% by area. Furthermore, the functional group equivalent was 171 g/eq.

(13)

[Structure of Formula (13)]

R = CH$_3$ or COOH

—Preparation of Composition—

A resin composition was prepared based on the blend (parts by mass) indicated in the following Table 1. As a result, epoxy resin compositions of Example 2 and Comparative Example 1 were obtained. The various components described in the table were as follows. Furthermore, in the table, a blank cell means "zero (0)".

(A-2) Epoxy resin: Epoxycyclohexane-containing silicone resin represented by the following Formula (14) (manufactured by Shin-Etsu Chemical Co., Ltd., X-40-2670)

(A-2) Epoxy resin: 3',4'-epoxycyclohexylmethyl 3,4-epoxycyclohexanecarboxylate (manufactured by Daicel Corp., CEL2021P)

(C) Curing accelerator: Quaternary phosphonium salt (manufactured by Nippon Chemical Industrial Co., Ltd., HISHICOLIN PX-4MP)

Oxidation inhibitor: Pentaerythritol tetrakis[3-(3',5'-di-t-butyl-4'-hydroxyphenyl)propionate] (manufactured by Adeka Corp., ADEKASTAB AO-60)

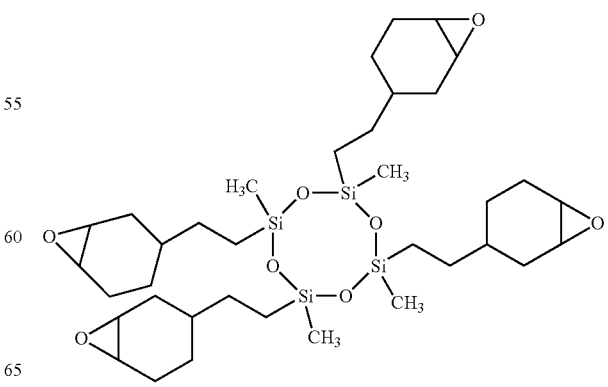

(14)

—Evaluation of Characteristics of Composition and Cured Product—

An evaluation of the characteristics of the compositions and cured products thus obtained was carried out by the following methods. Curing was performed by heating the composition for 1 hour at 100° C., and then for 4 hours at 150° C. The results are presented in Table 1.

(1) Viscosity

Viscosity was measured at 23° C. according to JIS K7233 using an E type rotational viscometer manufactured by Toki Sangyo Co., Ltd.

(2) Hardness

Hardness (type D) was measured according to JIS K6301 using a rod-shaped cured product.

(3) TMA (Tg, CTE)

TMA was measured using a specimen having a size of 5 mm×15 mm and a thickness of 4 mm, and using TMA/SS-6100 manufactured by SII Nanotechnology, Inc.

(4) Water Vapor Permeability

The water vapor permeability of each cured product having a thickness of 0.5 mm was measured according to JIS K7129.

TABLE 1

| Blend | | Example 2 | Comparative Example 1 |
|---|---|---|---|
| (A-1) Silicone-modified epoxy resin | Example 1 (A-1) | 50 | |
| (A-2) Epoxy resin | X-40-2670 | | 50 |
| (A-3) Epoxy resin | CEL2021P | 50 | 50 |
| (B) Curing agent | Synthesis Example 2 (B-1) | 72 | 89 |
| (C) Curing accelerator | PX-4MP | 0.5 | 0.6 |
| Oxidation inhibitor | ADEKASTAB0 AO-6 | 0.5 | 0.5 |
| Evaluation of characteristics | | | |
| Viscosity (23° C.) | Pa · s | 5.2 | 1.7 |
| Tg | ° C. | 163 | 168 |
| CTE1 | ppm | 70 | 73 |
| CTE2 | ppm | 171 | 135 |
| Flexural strength | MPa | 76 | 74 |
| Flexural modulus | N/mm$^2$ | 2500 | 2300 |
| Water vapor permeability | g/m$^2$ · 24 h, 0.5 mm thick | 3.8 | 5.8 |
| Hardness (Shore D) | — | 65 | 80 |

As is obvious from the results of Table 1, the composition of Example 2 has low gas permeability and excellent strength. On the other hand, the composition of Comparative Example 1 had excellent strength, but was inferior in low gas permeability.

What is claimed is:

1. A composition comprising a silicone-modified epoxy resin (A) represented by the following Formula (1):

$$\begin{array}{c}(1)\\ \text{[structure with } R^1, X, Si, O \text{ groups]}\end{array}$$

wherein R$^1$ represents a hydrocarbon group having 1 to 6 carbon atoms; X represents an organic group represented by the following Formula (2) or a hydrocarbon group having 1 to 6 carbon atoms; n represents an integer from 1 to 3; plural R$^1$s and plural Xs present in the formula may be respectively identical or different; and two or more of plural Xs represent an organic group represented by the following Formula (2):

$$-R^2-\!\!\!\!-(\ )_m\!\!\!\!-\!\!O \quad (2)$$

wherein R$^2$ represents an alkylene group having 2 to 3 carbon atoms; and m represents an integer from 0 to 2, and 3',4'-epoxycyclohexylmethyl 3,4-epoxycyclohexanecarboxylate.

2. The composition according to claim 1, wherein the silicone-modified epoxy resin is an addition reaction product between a compound represented by the following Formula (3) and a compound represented by the following Formula (4):

$$\begin{array}{c}(3)\\ \text{[structure with } R^1, Y, Si, O \text{ groups]}\end{array}$$

wherein R$^1$ and n respectively have the same meanings as defined above; each Y represents a hydrogen atom or a hydrocarbon group having 1 to 6 carbon atoms; plural R$^1$s and plural Ys present in Formula may be respectively identical or different; and two or more of plural Ys represent hydrogen atoms:

$$\begin{array}{c}(4)\\ \diagup\!\!\!\!-R^3-\!\!\!\!-(\ )_m\!\!\!\!-\!\!O\end{array}$$

wherein m has the same meaning as defined above; and R$^3$ represents a single bond or a methylene group.

3. The composition according to claim 1, wherein n is 2.

4. The composition according to claim 1, wherein the silicone-modified epoxy resin is obtained by oxidizing a polyvalent olefin-based compound represented by the following Formula (5):

$$\begin{array}{c}(5)\\ \text{[structure with } R^1, Z, Si, O \text{ groups]}\end{array}$$

wherein R$^1$ and n respectively have the same meanings as defined above; Z represents an organic group represented by the following Formula (6) or a hydrocarbon group having 1 to 6 carbon atoms; plural $R^1$s and plural Zs present in Formula may be respectively identical or different; and two or more of plural Zs represent an organic group represented by the following Formula (6):

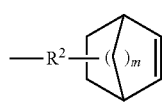

(6)

wherein $R^2$ and m respectively have the same meanings as defined above.

5. An epoxy resin composition comprising the (A) silicone-modified epoxy resin according to claim 1; 3′,4′-epoxycyclohexylmethyl 3,4-epoxycyclohexanecarboxylate; and (B) an epoxy resin curing agent.

6. An epoxy resin composition according to claim 5, wherein the epoxy resin curing agent according to claim 5 is at least one selected from amine-based curing agents, phenolic curing agents, acid anhydride-based curing agents, and polyvalent carboxylic acid resins.

7. A cured product obtained by curing the epoxy resin composition according to claim 5.

8. An epoxy resin composition comprising the (A) silicone-modified epoxy resin according to claim 1; 3′,4′-epoxycyclohexylmethyl 3,4-epoxycyclohexanecarboxylate; and (C) an epoxy resin curing accelerator.

\* \* \* \* \*